United States Patent [19]

Martin et al.

[11] 4,284,821
[45] Aug. 18, 1981

[54] DICHLOROVINYLCYCLOBUTANONES, PROCESSES FOR PREPARING THEM, AND THEIR USE AS INTERMEDIATES FOR PRODUCING PESTICIDAL COMPOSITIONS

[75] Inventors: Pierre Martin, Rheinfelden; Daniel Bellus, Riehen, both of Switzerland

[73] Assignee: Ciba-Geigy Corporation, Ardsley, N.Y.

[21] Appl. No.: 962,516

[22] Filed: Nov. 20, 1978

[30] Foreign Application Priority Data

Nov. 24, 1977 [CH] Switzerland ................. 14406/77
Oct. 26, 1978 [CH] Switzerland ................. 11076/78

[51] Int. Cl.³ ............... C07C 49/533; C07C 53/48
[52] U.S. Cl. ........................... 568/381; 568/364; 568/341; 260/544 Y; 260/347.4; 560/124; 562/506; 549/79; 424/275; 424/278; 424/305; 424/317
[58] Field of Search .......... 260/586 R, 544 Y, 586 C; 568/381

[56] References Cited

U.S. PATENT DOCUMENTS

| 3,395,174 | 7/1968 | Knell et al. | 260/544 Y |
| 3,400,101 | 9/1968 | Elam et al. | 260/586 R |
| 3,408,398 | 10/1968 | Martin | 260/586 R |
| 3,678,068 | 7/1972 | Anello et al. | 260/544 Y |
| 3,940,439 | 2/1976 | Harrow | 260/544 Y |

FOREIGN PATENT DOCUMENTS

| 858137 | 4/1977 | Belgium . | |
| 712616 | 6/1965 | Canada | 260/544 Y |
| 2539048 | 3/1976 | Fed. Rep. of Germany | 260/586 R |
| 2638356 | 3/1978 | Fed. Rep. of Germany | 260/586 R |
| 1420826 | 1/1965 | France | 260/586 R |
| 851684 | 10/1960 | United Kingdom | 260/544 Y |
| 1082808 | 9/1967 | United Kingdom . | |

OTHER PUBLICATIONS

Heine et al, "C.A." 88: 190209n, (1978).
Grandguillot et al., "C.A." 80: 82167y (1974).
Roedig et al., "C.A." 72: 31729k (1970).
Maahs, "C.A." 65: 10499h (1966).
Hubbard, "C.A." 67: 53583g (1967).
Vessieri, "C.A." 59: 13810c (13811d), (1963).
Neuse et al., "J. Org. Chem.", vol. 39, No. 11, (1974), pp. 1585-1587.

Primary Examiner—Joseph E. Evans
Assistant Examiner—James H. Reamer
Attorney, Agent, or Firm—Frederick H. Rabin

[57] ABSTRACT

Dichlorovinylcyclobutanones of the formula

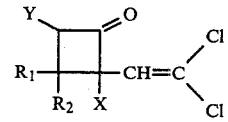

wherein one of $R_1$ and $R_2$ is methyl and the other is hydrogen or methyl, or $R_1$ and $R_2$ together are alkylene having 2-4 C atoms, X is chlorine and Y is hydrogen, or X is hydrogen and Y is chlorine; processes for preparing them, and their use as intermediates for producing pesticidal compositions.

3 Claims, No Drawings

DICHLOROVINYLCYCLOBUTANONES, PROCESSES FOR PREPARING THEM, AND THEIR USE AS INTERMEDIATES FOR PRODUCING PESTICIDAL COMPOSITIONS

The present invention relates to dichlorovinylcyclobutanones, and to a process for preparing them. The dichlorovinylcyclobutanones are intermediates for producing pesticidal compositions.

These dichlorovinylcyclobutanones correspond to the formula

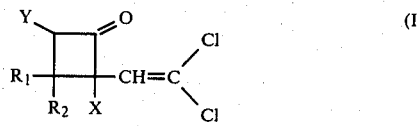

wherein
one of $R_1$ and $R_2$ is methyl and the other is hydrogen or methyl, or
$R_1$ and $R_2$ together are alkylene having 2–4 C. atoms,
X is chlorine and Y is hydrogen, or
X is hydrogen and Y is chlorine.

The new dichlorovinylcyclobutanones of the formula I can be produced by the process according to the invention by reacting a compound of the formula II

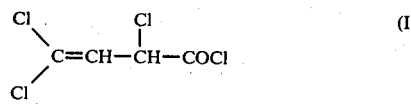

in the presence of an organic base, with a compound of the formula III

to give a compound of the formula Ia

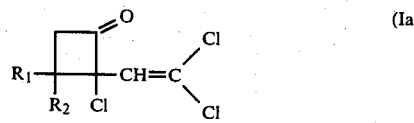

wherein $R_1$ and $R_2$ have the meanings defined under the formula I; and optionally rearranging the compound of the formula Ia, in the presence of a catalyst, to a compound of the formula I wherein X is hydrogen and Y is chlorine.

Preferred compounds of the formula I are those wherein $R_1$ and $R_2$ together are ethylene, and particularly compounds of the formula I wherein $R_1$ and $R_2$ are each methyl.

In the reaction of the acid chloride of the formula II in the presence of the organic base, there is intermediately formed a ketene of the formula IV

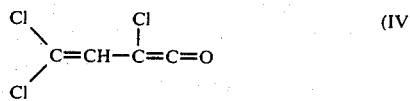

The ketone of the formula IV is new.

The reaction of the acid chloride of the formula II with the olefine of the formula III is advantageously performed in the presence of an inert organic solvent. Suitable inert organic solvents are for example optionally halogenated aromatic or aliphatic hydrocarbons, such as benzene, toluene, xylenes, chlorobenzene, dichloro- and trichlorobenzenes, n-pentane, n-hexane, n-octane, methylene chloride, chloroform, tetrachloromethane, 1,1,2,2-tetrachloroethane and trichloroethylene; cycloaliphatic hydrocarbons such as cyclopentane or cyclohexane; aliphatic or cycloaliphatic ketones such as acetone, methyl ethyl ketone, cyclopentanone and cyclohexanone; aliphatic and cyclic ethers such as diethyl ether, tetrahydrofuran, tetrahydropyrane and dioxane, and also nitriles of saturated aliphatic monocarboxylic acids having a total of 1–6 carbon atoms, such as acetonitrile, propionitrile, 3-methoxypropionitrile and butyronitrile.

Inert organic solvents preferred for this stage of the process are aliphatic, cycloaliphatic and aromatic hydrocarbons, particularly alkanes having 5–8 C atoms, benzene and toluene, more particularly however n-hexane and cyclohexane.

The reaction can be performed however also without the addition of an inert organic solvent, for example in excess olefine of the formula III.

Suitable organic bases are for example tertiary amines, especially trialkylamines having 1–4, particularly 2–4, carbon atoms in each of the alkyl moieties; cyclic amines such as pyridine, quinoline, N-alkylpyrrolidines, N-alkyl-piperidines, N,N'-dialkyl-piperazines and N-alkyl-morpholines or dialkylanilines having 1 or 2 carbon atoms in each of the alkyl moieties, such as N-methylpyrrolidine, N-ethylpiperidine, N,N'-dimethylpiperazine, N-ethylmorpholine and dimethylaniline, and also bicyclic amidines, such as 1,5-diazabicyclo-[5.4.0]-undec-5-ene and 1,5-diazabicyclo-[4.3.0]-non-5-ene, and bicyclic amino compounds, such as 1,4-diazabicyclo-[2.2.2]-octane.

Preferred bases are trialkylamines having 1–4 C atoms in each of the alkyl moieties, particularly triethylamine, and pyridine.

The organic base is used in at least the equimolar amount with respect to the acid chloride of the formula II, or alternatively in a slight excess.

The olefines of the formula III are used in at least the equimolar amount, relative to the acid chloride of the formula II, or to the ketone of the formula IV formed in situ. It is however in general advantageous to use an excess of olefine, and the olefine, as already mentioned, may also serve as solvent.

The reaction temperatures can vary within wide limits. The are generally between about 0° and 200° C., preferably between about 20° and 150° C.

The reaction can be performed by placing the compounds of the formulae II and III into the reaction vessel, and then adding dropwise the organic base; or by placing the olefine of the formula III into the reaction vessel and then adding dropwise, separately but simultaneously, the acid chloride and the organic base. Finally, it is also possible to place the organic base and the olefine into the reaction vessel, and to then add dropwise the acid chloride.

With readily volatile olefines of the formula III, it is also possible to perform the reaction under pressure.

After completion of the reaction, the compounds of the formula Ia can be optionally isolated in the customary manner, and if need be purified, for example by filtration and recrystallisation from suitable organic solvents, such as n-hexane.

For the rearrangement of the compounds of the formula Ia into compounds of the formula I wherein X is hydrogen and Y is chlorine, acids, bases or quaternary ammonium halides can be used as catalysts.

The rearrangement as defined is completely unexpected, and is known neither in the case of α-monohalogenated cyclobutanones specifically, nor in the case of α-monohalogenated ring ketones generally.

Suitable basic catalysts are organic bases, such as primary, secondary and in particular tertiary amines of the formula

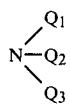

wherein
$Q_1$ is alkyl having 1–8 C atoms, cycloalkyl having 5 or 6 C atoms, benzyl or phenyl, and $Q_2$ and $Q_3$ independently of one another are hydrogen or alkyl having 1–8 C atoms, for example triethylamine, tri-n-butylamine, tri-isopentylamine, tri-n-octylamine, N,N-dimethyl-cyclohexylamine, N,N-dimethyl-benzylamine, N,N-dimethyl-2-ethylhexylamine or N,N-diethylaniline; also cyclic amines such as pyridine, quinoline or lutidine, N-alkylmorpholines such as N-methylmorpholine, N-alkylpiperidines such as N-methyl- and N-ethylpiperidine, N-alkylpyrrolidines such as N-methyl- and N-ethylpyrrolidine; diamines such as N,N,N',N'-tetramethylethylenediamine, N,N,N',N'-tetramethyl-1,3-diaminobutane, N,N'-dialkylpiperazines such as N,N'-dimethylpiperazine; bicyclic diamines such as 1,4-diazabicyclo[2.2.2]octane, and bicyclic amidines such as 1,5-diazabicyclo[5.4.0]undec-5-ene and 1,5-diazabicyclo[4.3.0]non-5-ene, and finally polymeric basic compounds, such as p-dimethylaminomethylpolystyrene and phosphines, especially trialkylphosphines, such as tributylphosphine.

Acid catalysts which can be used are for example inorganic or organic proton acids. Examples of suitable inorganic proton acids are hydrohalic acids, such as HCl, HBr, HF and HJ, nitric acid, phosphoric acid and sulfuric acid.

Suitable organic proton acids are for example: sulfinic acids such as benzenesulfonic acid; aliphatic and unsubstituted or substituted aromatic sulfonic acids, such as methanesulfonic acid, benzenesulfonic acid, p-toluenesulfonic acid, naphthalenesulfonic acid, naphthalene-1,5-disulfonic acids; aliphatic monocarboxylic acids preferably having 1–18 C atoms, such as formic acid, acetic acid, propionic acid, butyric acid, lauric acid, palmitic acid or stearic acid, halogen-containing monocarboxylic acids such as chloroacetic acid, dichloroacetic acid, trichloroacetic acid and trifluoroacetic acid; aliphatic dicarboxylic acids preferably having 2–12 C atoms, such as malonic acid, succinic acid, adipic acid or sebacic acid, aromatic mono- or dicarboxylic acids which can be substituted, such as benzoic acid, toluic acid, naphthoic acid, phthalic acid and terphthalic acid; aliphatic and aromatic phosphonic and phosphinic acids, such as methyl-, benzyl- or phenylphosphonic acid or dimethyl- and diethylphosphonic acid or diethyl- and benzenephosphinic acid.

If acids or bases are used in excess, they can also serve as solvents.

It is also possible to use salts of proton acids, particularly of hydrohalic acids, with ammonia or with a nitrogen-containing organic base, and also quaternary ammonium halides. Suitable organic bases containing nitrogen are aliphatic, cycloaliphatic, araliphatic and aromatic primary, secondary and tertiary amines as well as heterocyclic nitrogen bases. Examples which may be mentioned are: primary aliphatic amines having up to 12 C atoms, such as methylamine, ethylamine, n-butylamine, n-octylamine, n-dodecylamine, hexamethylenediamine, cyclohexylamine or benzylamine; secondary aliphatic amines having up to 12 C atoms, such as dimethylamine, diethylamine, di-n-propylamine, dicyclohexylamine, pyrrolidine, piperidine, piperazine or morpholine; tertiary aliphatic amines, particularly trialkylamines having 1–4 C atoms in each of the alkyl moieties, such as triethylamine, tri-n-butylamine, N-methylpyrrolidine, N-methylmorpholine or 1,4-diazabicyclo[2.2.2]octane; quinuclidine; unsubstituted or substituted primary, secondary and tertiary aromatic amines, such as aniline, toluidine, naphthylamine, N-methylaniline, diphenylamine and N,N-diethylaniline; also pyridine, picoline, indoline and quinoline.

Preferred salts are those of the formula

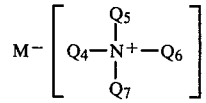

wherein
M is fluorine, bromine or iodine, especially chlorine,
$Q_4$ is hydrogen, alkyl having 1–18 C atoms, cyclohexyl, benzyl, phenyl or naphthyl, and
$Q_5$, $Q_6$ and $Q_7$ independently of one another are hydrogen or alkyl having 1–18 C atoms, and also N-alkyl-pyridinium halides having 1–18 C atoms in the alkyl moiety, particularly the corresponding chlorides.

Examples of salts of this type are: ammonium chloride, ammonium bromide, methylamine hydrochloride, cyclohexylamine hydrochloride, aniline hydrochloride, dimethylamine hydrochloride, diisobutylamino hydrochloride, triethylamine hydrochloride, triethylamine hydrobromide, tri-n-octylamine hydrochloride, benzyldimethylamine hydrochloride, tetramethyl-, tetraethyl-, tetra-n-propyl-, tetra-n-butylammonium chloride, -bromide and -iodide, trimethylhexadecylammonium chloride, benzyldimethylhexadecylammonium chloride, benzyldimethyltetradecylammonium chloride, benzyltrimethyl-, -triethyl- and -tri-n-butylammonium chloride, n-butyl-tri-n-propylammonium bromide, octadecyltrimethylammonium bromide, phenyltrimethylammonium bromide or chloride, hexadecylpyridinium bromide and chloride.

It is possible to use as additional co-catalysts alkali metal halides, such as potassium iodide, sodium iodide, lithium iodide, potassium bromide, sodium bromide, lithium bromide, potassium chloride, sodium chloride, lithium chloride, potassium fluoride, sodium fluoride and lithium fluoride.

These co-catalysts catalyse the reaction also in the absence of the above ammonium salts; in this case however additions of open-chain or macrocyclic polyethers (crown ethers) are of advantage in effecting a rapid course of reaction. Examples of crown ethers of this kind are: 15-crown-5, 18-crown-6, -dibenzo-18-crown-6, dicyclohexyl-18-crown-6, 5,6,14,15-dibenzo-7,13-diaza-1,4-dioxa-cyclopentadeca-5,14-diene.

The amount of catalyst used can vary within wide limits. In some cases it suffices if the catalyst is present in traces. In general, however, the catalyst is used in an amount of about 0.1 to 15 percent by weight, relative to the compound of the formula Ia.

The rearrangement can be performed both in the melt and in an inert organic solvent. The reaction temperature for the rearrangement in the melt is in general between about 60° and 200° C., particularly between about 80° and 170° C.

Suitable catalysts for the rearrangement reaction in the melt are in particular the aforementioned organic bases, especially trialkylamines having 1–8 C atoms in each of the alkyl moieties; also salts of hydrohalic acids with ammonia or with organic nitrogen-containing bases, such as trialkylamine hydrochlorides and -bromides having 1–8 C atoms in each of the alkyl moieties, and more especially tetraalkylammonium halides, above all tetraalkylammonium chlorides, bromides and iodides having 1–18 C atoms in each of the alkyl moieties.

Suitable inert organic solvents are for example:

optionally nitrited or halogenated aliphatic, cycloaliphatic or aromatic hydrocarbons, such as n-hexane, n-pentane, cyclohexane, benzene, toluene, xylenes, nitrobenzene, chloroform, carbon tetrachloride, trichloroethylene, 1,1,2,2-tetrachloroethane, nitromethane, chlorobenzene, dichlorobenzenes and trichlorobenzenes;

aliphatic and aromatic nitriles, such as alkyl nitriles having 2–5 C atoms, for example acetonitrile, propionitrile, butyronitrile and benzonitrile;

3-alkoxypropionitriles having 1 or 2 C atoms in the alkoxy moiety, such as 3-methoxypropionitrile and 3-ethoxypropionitrile;

aliphatic ketones having preferably a total of 3–8 C atoms, such as acetone, diethyl ketone, methyl-isopropyl ketone, diisopropyl ketone and methyl-tert-butyl ketone;

alkyl and alkoxyalkyl esters of aliphatic monocarboxylic acids having a total of 2–6 C atoms, such as formic acid methyl and ethyl esters, acetic acid methyl, ethyl, n-butyl and isobutyl esters, and also 1-acetoxy-2-methoxyethane;

cyclic ethers, such as tetrahydrofuran, tetrahydropyrane and dioxane;

dialkyl ethers having 1–4 C atoms in each of the alkyl moieties, such as diethyl ether, di-n-propyl ether and diisopropyl ether;

lower aliphatic alcohols, for example those having up to 6 C atoms, such as methanol, ethanol, propanol, isopropanol, butanols and pentanols;

aliphatic diols, such as ethylene glycol and diethylene glycol;

ethylene glycol and diethylene glycol mono- or dialkyl ethers having 1–4 C atoms in each of the alkyl moieties, such as ethylene glycol-monomethyl and -monoethyl ethers, diethylene glycol-monomethyl and -monoethyl ethers, ethylene glycol-dimethyl, -diethyl and -di-n-butyl ethers and diethylene glycol-diethyl and -di-n-butyl ethers;

N,N-disubstituted amides of aliphatic monocarboxylic acids having 1–3 C atoms in the acid moiety, such as N,N-dimethylformamide, N,N-dimethylacetamide, N,N-diethylacetamide, N-methyl-N-phenylacetamide and N,N-dimethylmethoxy-acetamide;

cyclic amides, such as n-methyl-2-pyrrolidone, N-acetyl-2-pyrrolidone and N-methyl-ε-caprolactam;

amides of carbonic acid, such as tetramethylurea and dimorpholinecarbonyl;

amides of phosphorous acid, of phosphoric acid, or phenylphosphoric acid or of aliphatic phosphonic acids having 1–3 C atoms in the acid moiety, such as phosphoric acid triamide, phosphoric acid tris-(dimethylamide) (hexametapol), phosphoric acid trimorpholide, phosphoric acid tripyrrolinide, phosphoric acid-bis-(dimethylamide)-morpholide, phosphoric acid dimethylamide-diethylamidemorpholide, phosphorous acid tris-(dimethylamide), and tetramethyldiamide of methanephosphonic acid;

amides of sulfuric acid, of aliphatic or aromatic sulfonic acids, such as tetramethylsulfamide, dimethylamide of methanesulfonic acid or p-toluenesulfonic acid amide; and sulfur-containing solvents, such as organic sulfones and sulfoxides, for example dimethylsulfoxide and sulfolane.

For the rearrangement reaction in the presence of an acid catalyst, it is advantageous to use polar solvents, particularly lower alcohols, such as methanol, ethanol and butanols, N,N-dialkylamides of aliphatic monocarboxylic acids having 1–3 C atoms in the acid moiety, especially N,N-dimethylformamide, or dialkylsulfoxides, such as dimethylsulfoxide.

In aprotic, strongly polar solvents, such as in the aforementioned N,N-disubstituted amides of aliphatic monocarboxylic acids, cyclic amides, amides of carbonic acid, amides of phosphorous acid, of phosphoric acid acid, of phenylphosphonic acid or of aliphatic phosphonic acids, amides of sulfur acid, of aliphatic or aromatic sulfonic acids, and also of dialkylsulfoxides, such as dimethylsulfoxide, the reaction proceeds also without the addition of a base. The solvent acts as catalyst in these cases.

In the case of the rearrangement reaction in the presence of an inert organic solvent as catalyst, there are however preferably used organic bases having a pKa value of above 9, particularly trialkylamines having 1–8 C atoms in each of the alkyl moieties, such as triethylamine, tri-n-butylamine and tri-n-octylamine; also hydrohalic acids, particularly HCl, and HBr, as well as tetraalkylammonium halides, especially tetraalkylammonium chlorides, bromides and iodides having 1–18 C atoms in each of the alkyl moieties.

Particularly preferred solvents are aliphatic alcohols having 2–4 C atoms, toluene, xylenes, chlorobenzene, dioxane, acetonitrile, 3-methoxypropionitrile, ethylene glycol diethyl ether and diisopropyl ketone.

The reaction temperatures for the rearrangement reaction in the presence of an inert organic solvent are in general between about 60° and 150° C., preferably between about 80° and 130° C.

After completion of the rearrangement reaction, the compounds of the formula I wherein X is H and Y is chlorine can be isolated in the customary manner, and optionally purified, for example by filtration, distillation and recrystallisation from suitable organic solvents, such as n-hexane.

The olefines of the formula III are known. The acid chloride of the formula II is new and is likewise subject matter of the present invention. The acid chloride of the formula II can be produced by treating a compound of the formula V

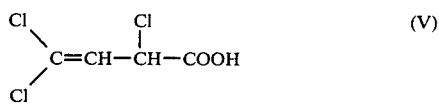 (V)

[produced according to 'Monatshefte der Chemie', 98, 2138 (1967)] with a chlorinating agent, such as phosphorus trichloride, phosphorus pentachloride, phosphorus oxychloride, oxalyl chloride, thionyl chloride, phosgene, benzoyl chloride or phthaloyl chloride.

The acid chloride of the formula II can also be produced by a process in which either carbon tetrachloride is caused to undergo an addition reaction, in the presence of a catalyst and in the presence of an organic solvent, with a compound of the formula VIa $$CH_2=CH-Z \quad \text{(VIa),}$$

or a compound of the formula VIb $$Cl_2CH-Z \quad \text{(VIb)}$$

is caused to undergo an addition reaction, in the presence of a catalyst and in the presence of an organic solvent, with 1,1-dichloroethylene, where Z is —COCl, —COOH, alkoxy carbonyl having 1-4 C atoms in the alkyl moiety, or —CN; and, if Z has a meaning other than —COCl, the resulting addition product of the formula VII

 (VII)

wherein

Z' is —COOH, alkoxy carbonyl having 1-4 C atoms in the alkyl moiety, or —CN, is converted into 2,4,4,4-tetrachlorobutyric acid chloride, and the 2,4,4,4-tetrachlorobutyric acid chloride is dehydrochlorinated to give the compound of the formula II.

The starting products (carbon tetrachloride, 1,1-dichloroethylene and compounds of the formulae VIa and VIb) are known. The reactants are used in at least the stoichiometric amount. Preferably, an excess of carbon tetrachloride or of compounds of the formula VIb is used, for example an approximately 0.5- to 2-fold molar excess, and the carbon tetrachloride can also serve as solvent.

Some of the intermediates of the formula VII are known [see J. Chem. Soc. 1887-96 (1963), Ann. Chim. Paris, 517–528 (1968), and also Israelian Patent Specification 18771=CA, 63, 13089e (1965)].

As catalysts for the addition reactions mentioned, there can be used compounds known per se, such as metals of the main group VIII and of the subgroups VIa, VIIa and Ib of the periodic system (according to the "Lehrbuch der anorgan. Chemie" [Textbook of Inorganic Chemistry], Holleman-Wiberg, W. de Gruyter+Co., Berlin), for example iron, cobalt, nickel, ruthenium, rhodium, palladium, chromium, molybdenum, manganese and copper. These metals can be used in the elementary form or in the form of compounds. Suitable compounds of this type are for example oxides, halides, sulfates, sulfites, sulfides, nitrates, acetates, citrates, carbonates, cyanides and rhodanides, and also complexes with ligands, such as phosphines, phosphites, benzoin, benzoyl- and acetylacetonates, nitriles, isonitriles and carbon monoxide. Examples which may be mentioned are: copper(II)oxide, iron(III)oxide; Cu(I)-, Cu(II)-, Fe(II)- and Fe(III)bromides and in particular -chlorides, as well as the chlorides of ruthenium, of rhodium, of palladium, of cobalt and of nickel; Cu(II)-sulfate, Fe(II)- and Fe(III)sulfate; Cu(II)-nitrate and iron(III)nitrate; manganese(III)acetate, copper(II)acetate, copper(II)stearate; iron(III)citrate; Cu(I)cyanide; ruthenium(II)dichloro-tris-triphenylphosphine, rhodium-tris(triphenylphosphine)chloride; chromium acetylacetonate and nickel acetylacetonate, copper(II)acetylacetonate, iron(III)acetylacetonate, cobalt(II)- and cobalt(III)acetylacetonate, manganese-(II)acetylacetonate, copper(II)benzoylacetonate; iron carbonylcyclopentadienyl complex; molybdenum carbonylcyclopentadienyl complex, chromium tricarbonylaryl complexes, ruthenium(II)acetato complex, chromium hexacarbonyl and molybdenum hexacarbonyl, nickel tetracarbonyl, iron pentacarbonyl, cobalt carbonyl and manganese carbonyl.

It is also possible to use mixtures of the stated metals with metal compounds and/or other additives, such as copper powder in combination with one of the aforementioned copper compounds; mixtures of copper powder with lithium halides, such as lithium chloride, or with isocyanides, such as tert-butylisocyanide; mixtures of iron powder with iron(III)chloride, optionally with the addition of carbon monoxide; mixtures of iron(III)-chloride and benzoin; mixtures of iron(II)- and iron-(III)chloride and trialkylphosphites; and mixtures of iron pentacarbonyl and iodine.

Preferred are iron(II)- and iron(III)salts and -complexes, and also iron powder, particularly however copper powder, copper(I)- and copper(II)salts and -complexes, such as Cu(I)chloride, Cu(II)chloride, Cu(I)bromide, Cu(II)bromide, Cu(II)acetylacetonate, Cu(II)benzoylacetonate, Cu(II)sulfate, Cu(II)nitrate and Cu(I)cyanide.

More especially preferred are copper powder, copper(I)- and copper(II)chloride or -bromide, and also mixtures thereof.

The stated catalysts are used in general in amounts of about 0.01 to 10 mol %, preferably 0.1 to 5 mol %, relative to the compound of the formula VIa or to 1,1-dichloroethylene.

The addition reactions described are performed in an organic solvent. Suitable organic solvents are those in which the catalysts are sufficiently soluble, or which can form complexes with the catalysts, which however are inert to the starting compounds. Examples of such solvents are alkyl nitriles, particularly those having 2-5 C atoms, such as acetonitrile, propionitrile and butyronitrile; 3-alkoxypropionitriles having 1 or 2 C atoms in the alkoxy moiety, such as 3-methoxypropionitrile and 3-ethoxypropionitrile; aromatic nitriles, especially benzonitrile; aliphatic ketones having preferably a total of 3-8 C atoms, such as acetone, diethyl ketone, methylisopropyl ketone, diisopropyl ketone, methyl-tert-butyl ketone; alkyl and alkoxyalkyl esters of aliphatic monocarboxylic acids having a total of 2-6 C atoms, such as formic acid methyl and ethyl esters, acetic acid methyl, ethyl, n-butyl and isobutyl esters, and also 1-acetoxy-2-methoxyethane; cyclic ethers such as tetrahydrofuran, tetrahydropyrane and dioxane; dialkyl ethers having 1-4 C atoms in each of the alkyl moieties, such as diethyl ether, di-n-propyl ether and diisopropyl ether; N,N-dialkylamides of aliphatic monocarboxylic acids having 1–3 C atoms in the acid moiety, such as N,N-dimethylformamide, N,N-dimethylacetamide, N,N-diethylacetamide and N,N-dimethylmethoxy-acetamide; ethylene glycol ether and diethylene glycol dialkyl ether having 1–4 C atoms in each of the alkyl moieties, such as ethylene glycol dimethyl ether, diethyl ether and di-n-butyl ether; diethylene glycol diethyl ether and di-n-butyl ether; and hexamethylphosphoric acid triamide (hexametapol).

Preferred solvents for the addition reaction are alkyl nitriles having 2–5 C atoms, and 3-alkoxypropionitriles having 1 or 2 C atoms in the alkoxy moiety, particularly acetonitrile and 3-methoxypropionitrile.

The reaction temperature is in general not critical and can vary within wide limits. The reaction temperatures are preferably between about 60° and 200° C., especially between about 80° and 170° C. The reaction can be performed under pressure or without pressure.

The compound of the formula VIa preferably used is acrylic chloride or acrylic acid. The intermediate of the formula VII with Z=—COOH, which is formed in the latter case, can be converted in a manner known per se by treatment with suitable chlorinating agents, for example those of the aforementioned type, into 2,4,4,4-tetrachlorobutyric acid chloride.

If there are used, as compound of the formula VIa or VIb, esters or nitriles as defined, the resulting intermediate of the formula VII can be hydrolysed in a manner known per se, in the presence of strong acids such as concentrated hydrochloric acid, to give 2,4,4,4-tetrachlorobutyric acid, whereupon this, as mentioned above, is converted, by treatment with suitable chlorinating agents, into 2,4,4,4-tetrachlorobutyric acid chloride.

Dichloroacetyl chloride is preferred as compound of the formula VIb.

The dehydrochlorination of the resulting 2,4,4,4-tetrachlorobutyric acid chloride to the acid chloride of the formula II can be performed in a manner known per se, advantageously in the presence of a Lewis acid, especially in the presence of iron(III)chloride or aluminium-(III)-chloride, at temperatures of between about 130° C. and 180° C., preferably between about 140° C. and 160° C.

The compounds of the formula I and II are valuable intermediates for producing pesticidal compositions. They can also be converted, by a new, totally unique, synthesis into pyrethroid-like pesticidal compositions or into precursors thereof. Compounds of this type, for example those of the formula VIII

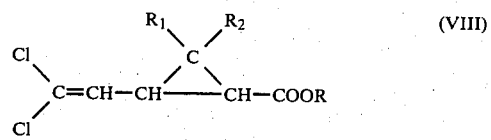

wherein $R_1$ and $R_2$ have the meanings defined under the formula I, and

R is hydrogen, alkyl having 1–4 C atoms, or a

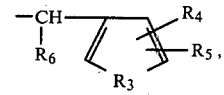

in which $R_3$ is —O—, —S— or —CH=CH—, $R_4$ is hydrogen, alkyl having 1–4 C atoms, benzyl, phenoxy or phenylmercapto, $R_5$ is hydrogen or alkyl having 1–4 C atoms, and $R_6$ is hydrogen or ethynyl or, if one of $R_1$ and $R_2$ is methyl and the other is hydrogen or methyl, $R_3$ is —CH=CH—, $R_4$ is phenoxy and $R_5$ is hydrogen, $R_6$ is also alkyl having 1–5 atoms, can be obtained by converting a compound of the formula I wherein X is H and Y is chlorine, in the presence of a base, for example of a compound of the formula IX

  (IX)

wherein

M is an alkali metal cation or alkaline-earth metal cation, and n is the number 1 or 2, and R has the meaning defined under the formula VIII, into a compound of the formula VIII.

Compared with prior known processes [see for example Farkas et al., Coll.Czech.Chem.Comm. 24, 2230 (1959) and Chem. Listy, 52, 688 (1958); British Pat. Specification No. 1,285,350; Belgian Pat. Specification No. 850,402; German Offenlegungsschriften Nos. 2,439,177, 2,539,895, 2,544,150, 2,547,510, 2,552,615, 2,554,380, 2,605,398, 2,615,159, 2,615,160, 2,616,528, 2,621,830, 2,621,832, 2,621,833, 2,621,835, 2,623,777, 2,630,981 and 2,639,777; U.S. Pat. No. 3,961,070 and Japanese Offenlegungsschriften 69872/76 and 47966/76], this new original method of synthesis is superior in that it is possible by its application to produce, by way of the new starting products of the formula II and the new compounds of the formula I, compounds of the formula VIII in a particularly simple and economic manner, in good to very good yields, and with high proportions of the desired cis form, which is especially effective in the case of specific applications. In contrast to the prior known processes, the process of the present invention has the advantage that the starting products are readily available, that the reagents used are comparatively cheap and ecologically favourable, and that all the reaction steps can be performed under relatively mild conditions and without any great expenditure on apparatus and on measures relating to safety. The compounds of the formulae I and Ia have the degree of oxidation necessary for their further employment, so that neither oxidation nor reduction reactions are required. The individual stages of the process can also be performed directly one after another without isolation of the respective intermediate, so that this synthesis method is very good for the large-scale commercial production of compounds of the formula VIII.

Compounds of the formula VIII wherein R is hydrogen or alkyl having 1–4 C atoms can be converted, in a manner known per se, into active substances of the formula VIII with R≠H or alkyl having 1–4 C atoms, or alternatively into compounds of the formula VIII wherein $R_6$ additionally denotes -CN, for example by reaction with corresponding halides or alcohols, optionally with prior conversion into the acid chloride, or by transesterification [see for example the German Offenlegungsschriften Nos. 2,553,991 and 2,614,648].

Compounds of the formula VIII with R≠H or alkyl having 1-4 C atoms are suitable for combating the widest variety of animal or plant pests, particularly as insecticides. The properties, fields of application and forms of application of these active substances are described in the literature [see Nature, 246, 169-70 (1973); Nature, 248, 710-11 (1974); Proceedings 7th British Insecticide and Fungicide Conference, 721-728 (1973); Proceedings 8th British Insecticide and Fungicide Conference, 373-78 (1975); J. Agr. Food Chem., 23, 115 (1975); U.S. Pat. No. 3,961,070; German Offenlegungsschriften Nos. 2,553,991, 2,439,177, 2,326,077 and 2,614,648].

EXAMPLE 1

(a) 244 g (1 mol) of 2,4,4,4-tetrachlorobutyric acid chloride with 0.25 g of iron(III)chloride is held at 160° C. for 1½ hours, in the course of which a vigorous evolution of hydrogen chloride is observed. The black reaction mixture is then distilled (87°-94° C./35 mm Hg). The distillate is redistilled through 0.25 ml of iron-(III)chloride to obtain 137 g (66% of theory) of 2,4,4-trichlorobut-3-enecarboxylic acid chloride; b.p. 80°-82° C./25 mm Hg.

IR spectrum (film) in $cm^{-1}$: 1800 (CO), 1625 (C=C).

NMR spectrum (100 MHz, $CDCl_3$) in ppm; 5.35 (d, J=10 Hz, 1H, CH); 6.15 (d, J=10 Hz, 1H, CH=C).

(b) 205.6 g (1.19 mols) of 2,4,4-trichlorobut-3-enecarboxylic acid [produced according to Monateshefte d. Chemie, 98, 2138 (1967)] is heated with 290 ml of thionyl chloride for 5 hours at 85° C. The reaction solution is concentrated by evaporation and subsequently distilled to obtain 209.7 g of 2,4,4-trichlorobut-3-enecarboxylic acid chloride; b.p. 75°-76° C./20 mm Hg. The spectroscopic data of the substance obtained agree with those of the products obtained according to (a).

The 2,4,4,4-tetrachlorobutyric acid chloride used according to (a) can be produced as follows: 452.5 g (5 mols) of acrylic chloride (commercial degree of purity), 1.5 liters of carbon tetrachloride, 1.5 liters of acetonitrile and 30 g of copper(I)chloride are held at 115° C. for 24 hours. The reaction mixture is filtered until clear, and concentrated in a water-jet vacuum. The residue is distilled to obtain 922 g (76% of theory) of 2,4,4,4-tetrachlorobutyric acid chloride, b.p. 78°-80° C./11 mm Hg.

IR spectrum ($CHCl_3$) in $cm^{-1}$: 1780 (CO).

NMR spectrum (100 MHz, $CDCl_3$) in ppm: 3.16-3.94 (m, 2H, $CH_2$); 4.84-4.96 (m, 1H, CH).

226 g (1 mol) of 2,4,4,4-tetrachlorobutyric acid [produced according to CA, 63, 13089e (1965)], 600 g of thionyl chloride and 1 ml of N,N-dimethylformamide are heated for 2 hours at 50° C. and for 2 hours at 75° C. After the unreacted thionyl chloride has been evaporated off, the residue is distilled to obtain 227.6 g (93% of theory) of 2,4,4,4-tetrachlorobutyric acid chloride; b.p. 90°-91° C./15 mm Hg.

145.9 g (1.5 mols) of 1,1-dichloroethylene, 147.4 g (1 mol) of dichloroacetyl chloride, 200 ml of acetonitrile and 3 g of copper(I)chloride are heated for 8 hours at 130° C. The reaction mixture is concentrated by evaporation and the residue is fractionally distilled. There is thus obtained 2,4,4,4-tetrachlorobutyric acid chloride as a colourless liquid; b.p. 78°-80° C./11 mm Hg.

EXAMPLE 2

166.4 g (0.8 mol) of 2,4,4-trichlorobut-3-enecarboxylic acid chloride in 1.6 liters of n-hexane is saturated with isobutylene. With stirring and whilst a weak stream of isobutylene is being introduced, there is then added dropwise at room temperature (20°-25° C.), in the course of 7 hours, 80.8 g (0.8 mol) of triethylamine. After subsequent stirring for one hour, the reaction mixture is filtered; the filtrate is then washed firstly with dilute sodium hydroxide solution, afterwards with dilute hydrochloric acid and finally with water; it is subsequently dried over magnesium sulfate and concentrated by evaporation. The residue is distilled to obtain 2-chloro-2-(2',2'-dichlorovinyl)-3,3-dimethylcyclobutanone, b.p. 54° C./0.1 mm Hg, as a colourless liquid.

IR spectrum ($CHCl_3$) in $cm^{-1}$: 1800 (CO), 1620 (C=C).

NMR spectrum (100 MHz, $CDCl_3$) in ppm: 1.38 (s, 3H, $CH_3$); 1.53 (s, 3H, $CH_3$); 2.77-3.29 (m, 2H, $CH_2$); 6.17 (s, 1s, C=CH).

Elementary analysis for $C_8H_9Cl_3O$ (molecular weight 227.52): calculated: C 42.23%, H 3.99%, Cl 46.75%; found: C 41.98%, H 3.85%, Cl 47.02%.

EXAMPLE 3

15.6 g (86.5 mMols) of the 2-chloro-2-(2',2'-dichlorovinyl)-3,3-dimethylcyclobutanone produced according to Example 2 and 5 g of tetrabutylammonium chloride are stirred together for 4 hours at 90° C. The cooled melt is taken up in n-hexane and filtered until clear. The filtrate which has been concentrated by evaporation is chromatographed on silica gel (elution with cyclohexane/toluene in the volume ratio of 1:1). There is thus obtained 2-(2',2'-dichlorovinyl)-3,3-dimethyl-4-chlorocyclobutanone as a colourless oil.

IR spectrum ($CDCl_3$) in $cm^{-1}$: 1780 (CO), 1670 (C=C).

NMR spectrum ($CDCl_3$, 100 MHz) in ppm: 1.10 (s, 3H, $CH_3$); 1.60 (s, 3H, $CH_3$); 3.98 (dd, J=8 Hz and 2 Hz, 1H, H-$C_2$); 4.73 (d, J=2 Hz, 1H, H-$C_4$); 5.80 (d, J=8 Hz, 1H, CH=$CCl_2$).

The above 2-(2',2'-dichlorovinyl)-3,3-dimethyl-4-chlorocyclobutanone can be converted as follows into compounds of the formula VIII:

A solution of 0.88 g (22 mMols) of solid sodium hydroxide in 40 ml of water is added to 4.55 g (20 mMols) of 2-(2',2'-dichlorovinyl)-3,3-dimethyl-4-chlorocyclobutanone, and the whole is stirred at room temperature for 25 hours. The solution, now clear, is washed with diethyl ether; it is subsequently rendered acid with semi-concentrated hydrochloric acid, and extracted with diethyl ether. The extract is washed with water, dried over magnesium sulfate and concentrated by evaporation. The residue is crystallised from n-hexane to yield the known cis-2-(2',2'-dichlorovinyl)-3,3-dimethylcyclopropanecarboxylic acid; m.p. 86°-87° C.

10 g (0.047 mol) of cis-2-(2',2'-dichlorovinyl)-3,3-dimethylcyclopropanecarboxylic acid is stirred in 100 ml of benzene with 12.1 ml (0.141 mol) of oxalyl chloride for 24 hours at room temperature. The reaction solution is concentrated by evaporation and the brown residue is distilled under reduced pressure to obtain 9.1 g of a clear liquid; b.p. 50° C./0.04 mm Hg. 3.0 g of this clear liquid is dissolved in 30 ml of toluene, and 2 ml of pyridine is added. There is then added dropwise at room temperature 2.9 g of α-cyano-m-phenoxybenzyl alcohol in 20 ml of toluene, and the reaction mixture is subsequently stirred for 16 hours at room temperature. The reaction mixture is washed firstly with water, then with saturated sodium hydrogen carbonate solution and finally with brine; it is afterwards dried over magnesium sulfate and concentrated by evaporation. The residue is chromatographed through silica gel (elution with diethyl ether/n-hexane 1:2). There is thus obtained pure cis-2-(2',2'-dichlorovinyl)-3,3-dimethylcyclopropanecarboxylic acid-α-cyano-m-phenoxybenzyl ester as a diastereoisomeric mixture.

NMR spectrum (60 MHz, CDCl$_3$) in ppm; 1.20–1.43 (m, 6H, 2×CH$_2$); 1.67–2.35 (m, 2H 2×CH); 6.25 (d, J=9 Hz, 1H, C$\underline{H}$=CCl$_2$); 6.40 and 6.45 (in each case 1s, in each case 0.5H, C$\underline{H}$—CN); 6.98–7.65 (m, 9H).

I claim:

1. A compound of the formula I

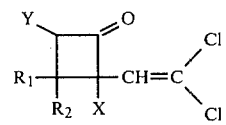

wherein
one of $R_1$ and $R_2$ is methyl and the other is hydrogen or methyl, or
$R_1$ and $R_2$ together are alkylene having 2–4 C atoms,
X is chlorine and Y is hydrogen, or
X is hydrogen and Y is chlorine.

2. A compound according to claim 1, wherein $R_1$ and $R_2$ are each methyl, or together are ethylene.

3. A compound according to claim 1, wherein $R_1$ and $R_2$ are each methyl.